United States Patent
Shum

(10) Patent No.: US 6,803,491 B1
(45) Date of Patent: Oct. 12, 2004

(54) PREPARATION OF LITHIUM PHOSPHATE CATALYSTS

(75) Inventor: Wilfred Po-sum Shum, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/712,284

(22) Filed: Nov. 13, 2003

(51) Int. Cl.$^7$ .................. C07C 33/02; B01J 27/18
(52) U.S. Cl. ............... 568/908; 568/386; 568/483; 502/208; 502/202; 502/214
(58) Field of Search ............... 502/202, 208, 502/214; 568/908, 386, 483

(56) References Cited

U.S. PATENT DOCUMENTS

| | | |
|---|---|---|
| 2,426,264 A | 8/1947 | Fowler et al. |
| 2,986,585 A | 5/1961 | Denton |
| 3,044,850 A | 7/1962 | Denton |
| 3,090,815 A | 5/1963 | Denton |
| 3,090,816 A | 5/1963 | Denton |
| 3,092,668 A | 6/1963 | Bruson et al. |
| 3,209,037 A | 9/1965 | Fourle |
| 3,238,264 A | 3/1966 | Rowton |
| 3,274,121 A | 9/1966 | Schneider |
| 4,065,510 A | 12/1977 | Schreyer |
| 4,342,666 A | 8/1982 | Hardy, Sr. |
| 4,720,598 A | 1/1988 | Scholte ............... 568/908 |
| 5,262,371 A | 11/1993 | Faraj ............... 502/78 |
| 5,292,974 A | 3/1994 | Faraj ............... 528/908 |
| 5,444,141 A | 8/1995 | Guo ............... 526/347 |
| 5,455,215 A | 10/1995 | Faraj ............... 502/214 |
| 5,475,073 A | 12/1995 | Guo ............... 526/333 |
| 5,600,033 A | 2/1997 | Faraj ............... 568/908 |
| 6,426,437 B1 | 7/2002 | Shum ............... 568/862 |

*Primary Examiner*—Elizabeth D. Wood
(74) *Attorney, Agent, or Firm*—Shao-Hua Guo

(57) ABSTRACT

A new method for preparing lithium phosphate catalysts is disclosed. The method comprises precipitating a lithium phosphate from a mixture comprising a first aqueous solution which contains lithium and sodium ions and a second aqueous solution which contains phosphate and borate ions. The resultant lithium phosphate catalyst has increased activity and selectivity in the isomerization of an alkylene oxide to the corresponding allylic alcohol.

25 Claims, No Drawings

PREPARATION OF LITHIUM PHOSPHATE CATALYSTS

FIELD OF THE INVENTION

The invention relates to lithium phosphate catalysts. More particularly, the invention relates to lithium phosphate catalysts that have increased activity for the isomerization of alkylene oxide to allylic alcohol.

BACKGROUND OF THE INVENTION

Lithium phosphate catalyst has been commercially used for the isomerization of propylene oxide to allyl alcohol. The catalyst was first disclosed in U.S. Pat. No. 2,426,264. The catalyst preparation involves precipitating a crude lithium phosphate from the mixture of an aqueous solution that contains phosphate ions and an aqueous solution that contains lithium ions. The crude precipitate is then washed with water and dried to form catalyst powder.

Methods for improving lithium phosphate catalysts are known. For example, U.S. Pat. No. 2,986,585 teaches the use of additional alkali metal hydroxides such as sodium hydroxide and potassium hydroxide during the precipitation of lithium phosphate. Although the function of the additional alkali metals in the lithium phosphate catalyst is not clear, the resultant catalyst has improved activity and selectivity for the alkylene oxide isomerization.

Allyl alcohol has been commercially used as an intermediate for the manufacture of 1,4-butanediol. See U.S. Pat. No. 6,426,437. It has also been increasingly used as a hydroxyl functional monomer in the polymer industry. For instance, allyl alcohol is used for making styrene-allyl alcohol copolymers (see U.S. Pat. No. 5,444,141) and hydroxyl acrylic resins (see U.S. Pat. No. 5,475,073).

It is apparent that improving the lithium phosphate catalyst is important to the industry. Ideally, the catalyst would have increased activity or productivity but would not incur increased cost.

SUMMARY OF THE INVENTION

The invention is a method for making lithium phosphate catalysts. The method comprises mixing a first aqueous solution which contains lithium and sodium ions and a second aqueous solution which contains phosphate and borate ions. A precipitate is then isolated from the mixture, and washed and dried to form lithium phosphate catalyst. The catalyst, which contains both boron and sodium, shows increased activity in the isomerization of an alkylene oxide to the corresponding allylic alcohol.

DETAILED DESCRIPTION OF THE INVENTION

The method of the invention comprises mixing a first aqueous solution which contains lithium and sodium ions and a second aqueous solution which contains phosphate and borate ions. The first solution is preferably prepared by dissolving in water a lithium compound and a sodium compound. Distilled water is preferred. Preferably, the lithium ion concentration is within the range of about 1.0 M to about 3.5 M. More preferably, the lithium ion concentration is within the range of about 1.5 M to about 3.0 M. Preferably, the sodium ion concentration is within the range of about 0.5 M to about 2.0 M. More preferably, the sodium ion concentration is within the range about 0.75 M to about 1.5 M.

Suitable lithium compounds include those which are soluble in water. Preferably, the lithium compounds are selected from the group consisting of lithium hydroxide, lithium nitrate, lithium acetate, and mixtures thereof. Lithium hydroxide is particularly preferred.

Unlike lithium compounds, all of sodium compounds are water soluble and thus suitable for the use in the invention. Preferably, the sodium compounds are selected from the group consisting of sodium hydroxide, sodium nitrate, sodium acetate, sodium carbonate, and mixtures thereof. Sodium hydroxide and its hydrates are particularly preferred.

The second solution is preferably prepared by dissolving in water a phosphate compound and a borate compound. Distilled water is preferred. Preferably, the phosphate ion concentration is within the range of about 0.5 M to about 1.5 M. More preferably, the phosphate ion concentration is within the range of about 0.5 M to about 1.0 M. Suitable phosphate compounds include those which are soluble in water. Preferably, the phosphate compounds are selected from the group consisting of sodium phosphates, potassium phosphates, ammonium phosphates and mixtures thereof. Sodium phosphates and their hydrates are particularly preferred.

Preferably, the borate ion concentration is within the range of about 0.5 M to about 2.5 M. More preferably, the borate ion concentration is within the range of about 1.0 M to about 2.0 M.

Suitable borate compounds include those which are soluble in water. Preferably, the borate compounds are selected from the group consisting of boric acid, sodium borates, potassium borates, ammonium borates and mixtures thereof. Boric acid, sodium borates and their hydrates are particularly preferred.

Preferably, both the first and the second solutions are heated, prior to mixing, to a temperature within the range of about 45° C. to about 95° C. More preferably, the solutions are heated to a temperature within the range of about 60° C. to about 80° C. The mixing is performed preferably with rapid stirring. It can be performed in a reactor or any suitable containers.

The ratio of the first and the second solutions is not critical. Preferably, the molar ratio of lithium ion/phosphate ion in the mixture is within the range of about 1/1 to about 6/1. More preferably, the ratio is within the range of about 211 to about 4/1.

Upon mixing, a crude lithium phosphate precipitates. The precipitate is then isolated and is washed with water. Washing is important. I have found that while the crude lithium phosphate has little catalytic activity in the isomerization of alkylene oxides, over-washed catalyst has diminished activity. Preferably, washing is so controlled that the washed lithium phosphate contains desirable amounts of sodium and boron.

The invention includes the lithium phosphate catalyst produced by the method of the invention. The catalyst has an increased activity and selectivity for the isomerization of alkylene oxides. The catalyst shows about 20–30% higher activity in the isomerization of propylene oxide to allyl alcohol than the catalyst which contains no boron. This translates into a significant cost savings and productivity increase of the commercial isomerization processes.

Preferably, the lithium phosphate of the invention contains from about 0.03 wt % to about 1 wt %, more preferably from about 0.1 wt % to about 0.8 wt %, of boron. Preferably, the lithium phosphate catalyst contains from about 0.01 wt % to about 1 wt %, more preferably from about 0.02 wt % to about 0.8 wt % of sodium.

Preferably, the lithium phosphate catalyst has a boron/lithium molar ratio within the range of 0.001 to about 0.05, more preferably within the range of about 0.003 to 0.03, and most preferably within the range of about 0.007 to about 0.02. Preferably, the lithium phosphate catalyst has a sodium/lithium molar ratio within the range of about 0.0002 to about 0.02, and more preferably within the range of 0.003 to about 0.01.

The invention also includes the use of the catalyst in the isomerization of alkylene oxides into corresponding allylic alcohols. More particularly, the catalyst is useful for the isomerization of propylene oxide to allyl alcohol or isobutene oxide into methallyl alcohol. I have found that the catalyst of the invention gives not only high catalytic activity but also maintains high selectivity for the isomerization of propylene oxide to allyl alcohol.

Isomerization processes are known, which include slurry and gas phase (also called vapor phase) processes. For instance, U.S. Pat. Nos. 2,426,264, 2,986,585, 3,044,850, 3,090,815, 3,090,816, 3,092,668, 3,209,037, 3,238,264, 3,274,121, and 4,342,666 teach slurry phase isomerization, and U.S. Pat. Nos. 4,065,510, 4,720,598, 5,262,371, 5,292,974, 5,455,215, and 5,600,033 teach gas phase isomerization. The teachings of these patents are incorporated herein by reference.

Slurry phase isomerization is preferred. In the slurry phase isomerization of propylene oxide, the lithium phosphate catalyst is suspended in a high-temperature oil and the vaporized propylene oxide passes through the catalyst slurry to form allyl alcohol. The propylene oxide conversion is usually used to evaluate the activity or efficiency of the catalyst, which is calculated by $$\text{Conversion (\%)} = \frac{\text{Propylene oxide reacted, wt}}{\text{Propylene oxide fed, wt}} \times 100$$

Several side reactions compete with the desired isomerization, leading to the formation of by-products such as propionaldehyde, acetone, n-propanol and acrolein. Selectivity of allyl alcohol formation, which measures the purity of allyl alcohol before separation, is calculated by $$\text{Selectivity (\%)} = \frac{\text{Allyl alcohol produced, wt}}{\text{Propylene oxide reacted, wt}} \times 100$$

Preferably, the isomerization of propylene oxide is performed at a temperature within the range of about 200° C. to about 300° C. More preferably, the isomerization temperature is within the range of about 240° C. to about 280° C. High isomerization temperature induces high catalyst activity. However, high temperature also decreases allyl alcohol selectivity. I have found that the catalyst of the invention maintains high activity at a relatively low isomerization temperature and therefore increases allyl alcohol selectivity without sacrificing the productivity.

The following examples further illustrate the invention. Examples 1 and 2 illustrate the preparation of the lithium phosphate catalysts that contain both sodium and boron. These catalysts give increased conversion of the isomerization of propylene oxide to allyl alcohol. In comparison, the catalysts in Comparative Examples 3 and 4, which do not contain either boron or sodium, show low propylene oxide conversion.

Comparative Examples 5 and 6 further show that adding boron to a potassium-containing catalyst does not increase the catalyst activity. Example 7 shows that the catalyst of the invention gives increased allyl alcohol selectivity at relatively low isomerization temperature while maintaining high propylene oxide conversion. Table 1 summarizes the differences of various catalysts.

Examples 8–17 and Comparative Examples 18–19 show the effect of boron and sodium concentrations in the lithium phosphate catalysts on the catalyst activity and allyl alcohol selectivity.

These examples merely illustrate the invention. Those skilled in the art will recognize many variations that are within the spirit of the invention and scope of the claims.

EXAMPLE 1

Lithium Phosphate Catalyst Containing both Sodium and Boron

Catalyst Preparation

In a first flask, 43.5 g of sodium phosphate dodecahydrate and 13 g of boric acid are dissolved in 150 ml of distilled water at 70° C. In a second flask, 15.8 g of lithium hydroxide hydrate ($LiOH.H_2O$) and 4.6 g of sodium hydroxide are dissolved in 125 ml of distilled water at 70° C. The solution in the first flask is then added to the second flask with rapid stirring for about 10 minutes at 70° C. A white precipitate of crude lithium phosphate is collected by filtration. The filtrate cake is broken down manually and stirred with 1.6 liters of distilled water in a 2 liter flask at 85–90° C. for 1.5 hours. The white powder is collected by filtration, and then dried overnight in a vacuum oven at 130° C. The resultant catalyst contains about 0.1–0.3 wt % of sodium and 0.3–0.5 wt % of boron.

Isomerization of Propylene Oxide

The isomerization is performed in a glass reactor. The bottom of the is reactor is a glass tube which has 1.5" ID and 7" in height. The glass tube is connected to a 250 cc round flask. The flask is fitted with a condenser which is connected to a 250 cc receiving flask. The receiving flask is kept at a temperature of 10° C. or lower. The bottom glass tube has a porous frit for the entrance of the propylene oxide which is introduced from an ISCO pump. The lithium phosphate catalyst slurry (7 g of catalyst in 65 g of Therminol™-55 heat transfer fluid (product of Solutia, Inc.)) is charged into the glass tube. Propylene oxide is vaporized in a preheating zone prior to its contact with the lithium phosphate catalyst. The reaction is performed at 273° C. by continuously feeding propylene oxide at a rate of 20 cc per hour. Samples are periodically collected and analyzed by GC for the propylene oxide conversion and the product selectivity. The propylene oxide conversion is within the range of 53.5% to 59.2%. The allyl alcohol selectivity is within the range of 92.7% to 93.0%.

EXAMPLE 2

Lithium Phosphate Catalyst Containing both Sodium and Boron

The general procedure of Example 1 is repeated except in the first flask, 43.5 g of sodium phosphate dodecahydrate and 20 g of sodium tetraborate decahydrate are dissolved. The resultant lithium phosphate catalyst contains 0.1–0.3 wt % of sodium and 0.3–0.6 wt % of boron. The propylene oxide conversion is within the range of 54.0% to 58.7% and the allyl alcohol selectivity is within the range of 92.8% to 93.0%.

COMPARATIVE EXAMPLE 3

Lithium Phosphate Catalyst Containing Sodium But No Boron

The general procedure of Example 1 is repeated except in the first flask, 43.5 g of sodium phosphate dodecahydrate is dissolved in 150 ml of distilled water but no borate is used. The propylene oxide conversion is within the range of 41.0% to 43.8%. The allyl alcohol selectivity is within the range of 92.6% to 92.9%.

COMPARATIVE EXAMPLE 4

Lithium Phosphate Catalyst Containing Boron But No Sodium

The general procedure of Example 1 is repeated except in the first flask, 13.3 g of 85% phosphoric acid and 10 g of boric acid are dissolved in 150 ml of distilled water; in the second flask, 19.4 g of $LiOH.H_2O$ is dissolved in 300 ml of distilled water. The resultant lithium phosphate catalyst contains 0.3 wt % of boron. The propylene oxide conversion is within the range of 20.5 to 23.6%. The allyl alcohol selectivity is within the range of 90.1% to 90.3%.

COMPARATIVE EXAMPLE 5

Lithium Phosphate Catalyst Containing Potassium But No Sodium and Boron

The general procedure of Example 1 is repeated except in the first flask, 21.5 g of KOH and 14.6 g of 85% phosphoric acid are dissolved in 150 ml of distilled water and in the second flask, 16.0 g of $LiOH.H_2O$ and 6.7 g of KOH are dissolved in 125 ml of distilled water. The resultant lithium phosphate catalyst contains about 0.1–0.2% of potassium. The propylene oxide conversion is within the range of 42.2% to 44.5% and allyl alcohol selectivity within the range of 92.7% to 92.9%.

COMPARATIVE EXAMPLE 6

Lithium Phosphate Catalyst Containing Potassium and Boron But No Sodium

The general procedure of Comparative Example 4 is repeated except in the second flask, 15.8 g of $LiOH.H_2O$ and 6.4 g of KOH are dissolved in 125 ml of distilled water. The resultant lithium phosphate catalyst contains 0.1 wt % of potassium and 0.3 wt % of boron. The propylene oxide conversion is within the range of 42.4% to 45.8% and allyl alcohol selectivity within the range of 92.4% to 92.7%.

EXAMPLE 7

Isomerization at Low Temperature with Lithium Phosphate Catalyst Containing Both Sodium and Boron The general procedure of Example 1 is repeated but the isomerization is performed at 253° C. The propylene oxide conversion is within the range of 39.9% to 42.5% and allyl alcohol selectivity is within the range of 93.6% to 94%.

EXAMPLES 8–17 AND COMPARATIVE EXAMPLES 18 AND 19

The Effect of Boron and Sodium Concentrations on the Catalyst Activity and Allyl Alcohol Selectivity The general procedure of Example 1 is repeated by varying the amounts of sodium phosphate, boric acid, lithium hydroxide and sodium hydroxide or varying the washing procedure to obtain lithium phosphate catalysts having different amounts of boron and sodium. These examples show the effects of the concentrations of boron and sodium and the ratios of boron/lithium and sodium/lithium on the isomerization of propylene oxide to allyl alcohol. The lithium, boron and sodium concentrations are measured by element analysis. The results are listed in Table 2.

TABLE 1

Comparing Various Lithium Phosphate Catalysts in the Isomerization of Propylene Oxide to Allyl Alcohol

| Ex. No. | Catalyst | Containing Boron | Containing Sodium | Containing Potassium | Propylene Oxide Conversion | Allyl Alcohol Selectivity |
|---|---|---|---|---|---|---|
| 1 | Lithium Phosphate | Yes | Yes | No | 53.5%–59.2% | 92.7%–93.0% |
| 2 | Lithium Phosphate | Yes | Yes | No | 54.0%–58.7% | 92.8%–93.0% |
| C3 | Lithium Phosphate | No | Yes | No | 41.0%–43.8% | 92.6%–92.9% |
| C4 | Lithium Phosphate | Yes | No | No | 20.5%–23.6% | 90.1%–90.3% |
| C5 | Lithium Phosphate | No | No | Yes | 42.2%–44.5% | 92.7%–92.9% |
| C6 | Lithium Phosphate | Yes | No | Yes | 42.4%–45.8% | 92.4%–92.7% |

TABLE 2

Effect of Boron and Sodium Concentrations on Isomerization of Propylene Oxide

| Ex. No. | Sodium wt % | Sodium/lithium Molar Ratio | Boron wt % | Boron/lithium Molar Ratio | Propylene* Oxide Conversion | Allyl Alcohol* Selectivity |
|---|---|---|---|---|---|---|
| 8 | 0.22 | 0.00374 | 0.42 | 0.0152 | 59.2% | 93.0% |
| 9 | 0.16 | 0.00271 | 0.34 | 0.0123 | 57.2% | 92.7% |
| 10 | 0.31 | 0.00528 | 0.54 | 0.0196 | 55.8% | 93.0% |
| 11 | 0.06 | 0.00102 | 0.59 | 0.0212 | 55.0% | 92.4% |
| 12 | 0.05 | 0.00085 | 0.43 | 0.0155 | 54.9% | 92.5% |
| 13 | 0.08 | 0.00136 | 0.29 | 0.0105 | 48.0% | 92.4% |
| 14 | 0.03 | 0.00051 | 0.20 | 0.0072 | 49.8% | 92.1% |
| 15 | 0.02 | 0.00034 | 0.32 | 0.0115 | 48.1% | 92.0% |
| 16 | 0.65 | 0.0111 | 0.65 | 0.0236 | 48.7% | 92.6% |
| 17 | 0.66 | 0.0113 | 0.85 | 0.0310 | 45.3% | 92.4% |
| C18 | 1.7 | 0.0296 | 1.2 | 0.0444 | 20.8% | 90.5% |
| C19 | 1.7 | 0.0297 | 1.4 | 0.0520 | 12.5% | 91.1% |

*Average value

I claim:

1. A method comprising precipitating a lithium phosphate from a mixture comprising a first aqueous solution containing lithium and sodium ions and a second aqueous solution containing phosphate and borate ions, isolating the precipitate, and washing and drying the precipitate to form a lithium phosphate catalyst.

2. The method of claim 1 wherein the first solution is prepared by dissolving in water a lithium compound selected from the group consisting of lithium hydroxide, lithium nitrate, lithium acetate, and mixtures thereof and a sodium compound selected from the group consisting of sodium hydroxide, sodium nitrate, sodium acetate, sodium carbonate, and mixtures thereof.

3. The method of claim 2 wherein the lithium compound is lithium hydroxide.

4. The method of claim 2 wherein the sodium compound is sodium hydroxide.

5. The method of claim 2 wherein the lithium compound is lithium hydroxide and the sodium compound is sodium hydroxide.

6. The method of claim 1 wherein the second solution is prepared by dissolving in water a phosphate compound selected from the group consisting of sodium phosphates, potassium phosphates, ammonium phosphates, and mixtures thereof and a borate compound selected from the group consisting of boric acid, sodium borates, potassium borates, ammonium borates, and mixtures thereof.

7. The method of claim 6 wherein the phosphate compound is a sodium phosphate.

8. The method of claim 6 wherein the borate compound is boric acid or a sodium borate.

9. The method of claim 6 wherein the phosphate compound is a sodium phosphate and the borate compound is a sodium borate.

10. The method of claim 1 wherein the first and the second solutions are heated, prior to mixing, to a temperature within the range of about 45° C. to about 95° C.

11. The method of claim 10 wherein the temperature is within the range of about 60° C. to about 80° C.

12. A lithium phosphate catalyst which contains effective amounts of boron and sodium to enhance the catalyst activity and selectivity for an isomerization of alkylene oxide to allylic alcohol.

13. The catalyst of claim 12 which contains from about 0.03 wt % to about 1 wt % of boron.

14. The catalyst of claim 12 which contains from about 0.1 wt % to about 0.8 wt % of boron.

15. The catalyst of claim 12 which contains from about 0.01 wt % to about 1 wt % of sodium.

16. The catalyst of claim 12 which contains from about 0.02 wt % to about 0.8 wt % of sodium.

17. The catalyst of claim 12 which has a boron/lithium molar ratio within the range of about 0.001 to about 0.05.

18. The catalyst of claim 12 which has a boron/lithium molar ratio within the range of about 0.003 to 0.03.

19. The catalyst of claim 12 which has a boron/lithium molar ratio within the range of about 0.007 to about 0.02.

20. The catalyst of claim 12 which has a sodium/lithium molar ratio within the range of about 0.0002 to about 0.02.

21. The catalyst of claim 12 which has a sodium/lithium molar ratio within the range of 0.003 to about 0.01.

22. A process comprising isomerizing propylene oxide to allyl alcohol in the presence of a lithium phosphate catalyst which contains effective amounts of boron and sodium.

23. The process of claim 22 wherein the isomerizing is performed in slurry phase.

24. The process of claim 22 wherein the isomerizing is within the range of 200° C. to about 300° C.

25. The process of claim 22 wherein the isomerizing is within the range of about 240° C. to about 280° C.

* * * * *